United States Patent [19]

Ehrenfreund

[11] Patent Number: 5,187,197
[45] Date of Patent: Feb. 16, 1993

[54] PHENYLTHIOUREAS, PHENYLISOTHIOUREAS AND PHENYLCARBODIIMIDES, COMPOSITIONS, CONTAINING THEM AND THEIR USE IN THE CONTROL OF PESTS

[75] Inventor: Josef Ehrenfreund, Allschwil, Switzerland

[73] Assignee: Ciba-Geigy Corporation, Ardsley, N.Y.

[21] Appl. No.: 570,195

[22] Filed: Aug. 20, 1990

Related U.S. Application Data

[62] Division of Ser. No. 231,749, Aug. 12, 1988, Pat. No. 4,968,720.

[30] Foreign Application Priority Data

Aug. 20, 1987 [CH] Switzerland ............ 3197/87-4
Mar. 3, 1988 [CH] Switzerland ............ 790/88-6

[51] Int. Cl.$^5$ ............... A01N 47/28; C07C 335/00
[52] U.S. Cl. ............... 514/585; 564/26; 564/28; 564/29; 514/507
[58] Field of Search ............... 564/26, 28, 29; 514/585, 587

[56] References Cited

U.S. PATENT DOCUMENTS 4,897,424  1/1930  Böger et al. ............... 564/26

FOREIGN PATENT DOCUMENTS

| 0888179 | 3/1981 | Belgium ............... 564/26 |
| 0296120 | 6/1987 | European Pat. Off. ............... 564/26 |
| 0282452 | 9/1988 | European Pat. Off. ............... 564/26 |
| 0304402 | 2/1989 | European Pat. Off. ............... 564/26 |
| 3801395 | 8/1988 | Fed. Rep. of Germany ............... 564/26 |

OTHER PUBLICATIONS

J. Chem. Soc. (C) 1967, pp. 1780-1782.

*Primary Examiner*—Mary C. Lee
*Assistant Examiner*—Robert C. Whittenbaugh
*Attorney, Agent, or Firm*—Edward McC. Roberts

[57] ABSTRACT

Novel substituted phenyl-thioureas, -isothioureas and -carbodiimides of formula I

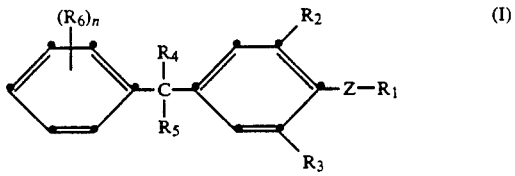

in which $R_1$ is $C_1$-$C_8$alkyl, $C_1$-$C_8$alkyl mono- or polysubstituted by halogen and/or by $C_1$-$C_6$alkoxy, $C_3$-$C_8$cycloalkyl, $C_3$-$C_8$cycloalkyl mono- or poly-substituted by $C_1$-$C_3$alkyl, or is $C_3$-$C_8$cycloalkyl-$C_1C_4$alkyl; each of $R_2$ and $R_3$ is $C_1$-$C_6$alkyl, $C_5$-$C_6$cycloalkyl or $C_5$-$C_6$cycloalkenyl; each of $R_4$ and $R_5$ is hydrogen or $C_1$-$C_4$alkyl; each $R_6$ is halogen, $C_1$-$C_4$alkyl, $C_1$-$C_4$alkoxy, $C_1$-$C_4$haloalkyl, $C_1$-$C_4$haloalkoxy or a $-(CH=CH)_2$, $-(CH_2)_3$ or $-(CH_2)_4$ bridge in the 2,3- or 3,4-position; n is 0, 1 or 2; Z is —NH—CS—NH—, —N=C(SR$_7$)—NH— or —N=C=N—, and $R_7$ is $C_1$-$C_{10}$alkyl or $C_3$-$C_5$alkenyl, and salts thereof with organic or inorganic acids, processes and intermediates for their manufacture, their use in the control of pests, and pesticidal compositions that contain at least one compound of formula I as active ingredient, are disclosed. The preferred field of use is the control of pests in and on animals and plants.

11 Claims, No Drawings

PHENYLTHIOUREAS, PHENYLISOTHIOUREAS AND PHENYLCARBODIIMIDES, COMPOSITIONS, CONTAINING THEM AND THEIR USE IN THE CONTROL OF PESTS

This is a divisional of application Ser. No. 231,749 filed on Aug. 12, 1988 now U.S. Pat. No. 4,968,720.

The present invention relates to novel substituted phenyl-thioureas, -isothioureas and -carbodiimides, to their salts with organic and inorganic acids, to processes and intermediates for their preparation, to pesticidal compositions that contain these compounds, and to their use in the control of pests.

The compounds according to the invention correspond to formula I

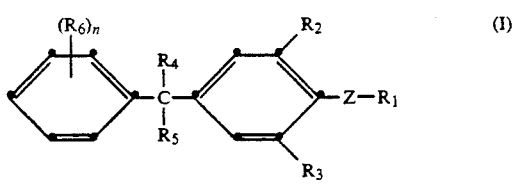

in which $R_1$ is $C_1$–$C_8$alkyl, $C_1$–$C_8$alkyl mono- or poly-substituted by halogen and/or by $C_1$–$C_6$alkoxy, $C_3$–$C_8$-cycloalkyl, $C_3$–$C_8$cycloalkyl mono- or poly-substituted by $C_1$–$C_3$alkyl, or is $C_3$–$C_8$cycloalkyl-$C_1$–$C_4$alkyl; each of $R_2$ and $R_3$ is $C_1$–$C_6$alkyl, $C_5$–$C_6$cycloalkyl or $C_5$–$C_6$-cycloalkenyl; each of $R_4$ and $R_5$ is hydrogen or $C_1$–$C_4$alkyl; each $R_6$ is halogen, $C_1$–$C_4$alkyl, $C_1$–$C_4$alkoxy, $C_1$–$C_4$haloalkyl, $C_1$–$C_4$haloalkoxy or a $-(CH=CH)_2$-, $-(CH_2)_3$- or $-(CH_2)_4$- bridge in the 2,3- or 3,4-position; n is 0, 1 or 2; Z is —NH—CS—NH—, —N=C(SR$_7$)—NH— or —N=C=N—, and $R_7$ is $C_1$–$C_{10}$alkyl or $C_3$–$C_5$alkenyl.

Halogen atoms coming into consideration as substituents are fluorine and chlorine as well as bromine and iodine, fluorine and chlorine being preferred. Alkyl radicals coming into consideration as substituents may be straight-chain or branched. Examples of such alkyl radicals that may be mentioned are methyl, ethyl, propyl, isopropyl, butyl, isobutyl, sec-butyl, tert-butyl or pentyl, hexyl, octyl etc. and the isomers thereof.

Alkenyl radicals coming into consideration as substituents may be straight-chain or branched and may have one or more double bonds. Examples of such alkenyl radicals are, inter alia, allyl, 1-propenyl, isopropenyl, allenyl, butenyls or pentenyls.

The $C_1$–$C_8$alkyl radicals mono- or poly-substituted by halogen and/or by $C_1$–$C_6$alkoxy that come into consideration as substituents may be straight-chain or branched and may be only partially halogenated or perhalogenated and/or substituted from one to five times by $C_1$–$C_6$alkoxy, the above definitions applying to the halogen atoms and alkyl radicals. Suitable examples of such substituents are, inter alia, methyl mono- to tri-substituted by fluorine, chlorine and/or by bromine, such as, for example, $CHF_2$ or $CF_3$; ethyl substituted from one to five times by fluorine, chlorine and/or by bromine, such as, for example, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or by bromine, such as, for example, $CH_2CHBrCH_2Br$, $CF_2CHFCF_3$, $CH_2CF_2CF_3$ or $CH(CF_3)_2$; butyl, or one of the isomers thereof, substituted from one to nine times by fluorine, chlorine and/or by bromine, such as, for example, $CF(CF_3)CHFCF_3$ or $CH_2(CF_2)_2CF_3$; methoxymethyl, methoxyethyl, ethoxyethyl, methoxypropyl, ethoxypropyl, propoxypropyl, methoxybutyl, ethoxybutyl, propoxybutyl or butoxybutyl, 1,2-dimethoxyethyl, 1,3-dimethoxypropyl or 2,4-dimethoxybutyl. The above also applies analogously to the optionally mono- or poly-halogenated $C_1$–$C_4$alkyl and $C_1$–$C_4$alkoxy radicals and to the unsubstituted $C_1$–$C_4$alkoxy radicals.

Cycloalkyl and cycloalkenyl radicals coming into consideration as substituents are, for example, cyclopropyl, cyclobutyl, cyclopentyl, cyclopentenyl, cyclohexyl or cyclohexenyl. The cycloalkyl radicals may be mono- or poly-substituted by a $C_1$–$C_4$alkyl radical and/or bonded via a $C_1$–$C_4$alkylene bridge to the rest of the molecule. The compounds of formula I in which Z is —N=C(SR$_7$)—NH— can also be in the form of acid addition salts. Both organic and inorganic acids are suitable for the formation of such salts. Examples of such acids are, inter alia, hydrochloric acid, hydrobromic acid, hydriodic acid, nitric acid, various phosphoric acids, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acids or salicylic acid.

Compounds of formula I in which Z is —N=C(SR$_7$)—NH— can be in the tautomeric forms

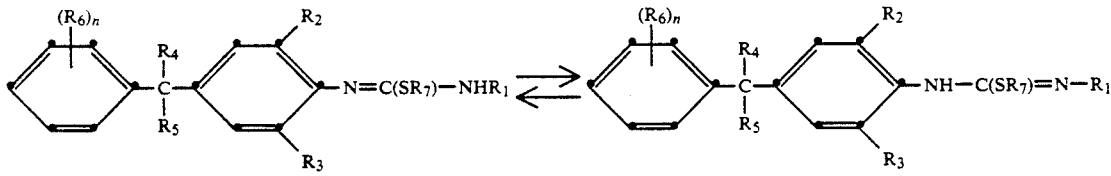

The invention includes both the individual tautomers and tautomeric mixtures.

Depending on the value of n, the benzyl radical may be substituted several times by $R_6$. When n is greater than 1, the various $R_6$ radicals may have the same or different meanings.

Compounds of formula I that are of particular importance are those in which $R_1$ is $C_1$–$C_6$alkyl, $C_1$–$C_6$alkyl mono- or poly-substituted by halogen and/or by $C_1$–$C_3$alkoxy, or $C_5$–$C_6$cycloalkyl; each of $R_2$ and $R_3$ is $C_1$–$C_5$alkyl or $C_5$–$C_6$cycloalkyl; each of $R_4$ and $R_5$ is hydrogen or $C_1$–$C_3$alkyl; $R_6$ is halogen, methyl, methoxy, trifluoromethyl or trifluoromethoxy; n is 0 or 1; Z is —NH—CS—NH—, —N=C(SR$_7$)—NH— or —N=C=N—; and $R_7$ is $C_1$–$C_6$alkyl or $C_3$–$C_4$alkenyl.

Preferred are those compounds of formula I in which $R_1$ is $C_1$–$C_5$alkyl or cyclopentyl; each of $R_2$ and $R_3$ is $C_3$–$C_5$alkyl or $C_5$–$C_6$cycloalkyl; each of $R_4$ and $R_5$ is hydrogen or methyl; $R_6$ is fluorine, chlorine or methyl; n is 0 or 1; Z is —NH—CS—NH—, —N=C(SR- 7) —NH— or —N=C=N—; and $R_7$ is $C_1$-$C_3$alkyl or allyl. Of particular importance are those compounds of formula I in which a) $R_1$ is $C_3$-$C_5$alkyl or cyclopentyl; each of $R_2$ and $R_3$ is $C_3$-$C_5$alkyl; each of $R_4$ and $R_5$ is hydrogen or methyl; n is 0; and Z is —NH—CS—NH—; or b) $R_1$ is $C_3$-$C_5$alkyl or cyclopentyl; each of $R_2$ and $R_3$ is $C_3$-$C_5$alkyl; each of $R_4$ and $R_5$ is hydrogen or methyl; n is 0; Z is —N=C(SR_7)—NH—; and $R_7$ is $C_1$-$C_2$alkyl; or c) $R_1$ is $C_3$-$C_5$alkyl or cyclopentyl; each of $R_2$ and $R_3$ is $C_3$-$C_5$alkyl; each of $R_4$ and $R_5$ is hydrogen or methyl; n is 0; and Z is —N=C=N—.

The compounds of formula I according to the invention can be prepared according to processes that are known in principle, for example by reacting A) an isothiocyanate of formula II

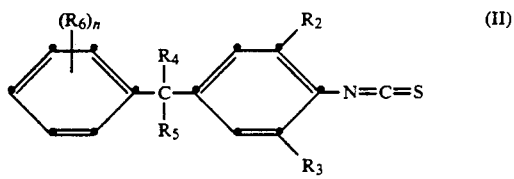

with an amine of formula III $$H_2N-R_1 \qquad (III)$$

to form the thiourea and optionally

B) reacting the resulting thiourea with a compound of formula IV $$X-R_7 \qquad (IV)$$

to form the isothiourea, or

C) converting the resulting thiourea into the carbodiimide by removal of hydrogen sulfide. $R_1$, $R_2$, $R_3$, $R_4$, $R_5$, $R_6$, $R_7$ and n have the meanings given and X is a suitable leaving group, such as, for example, a halogen atom, especially chlorine, bromine or iodine, or an unsubstituted or halogenated or alkylated sulfate, such as, for example, a tosylate, brosylate or mono- or di-alkyl sulfate (mesylate, dimethyl sulfate).

Process A is customarily carried out under normal pressure and in the presence of an organic solvent or diluent. The temperature is from 0° to +150° C., preferably from +10° to 70° C. As solvents and diluents there are suitable, for example, ethers and ethereal compounds, such as diethyl ether, dipropyl ether, dibutyl ether, dioxane, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; ketones, such as acetone, methyl ethyl ketone, methyl isopropyl ketone, methyl isobutyl ketone or cyclohexanone.

Process B is advantageously carried out in an inert organic solvent and under slightly elevated or normal pressure. The temperature is from +10° to 250° C., preferably the boiling temperature of the solvent used or from +50° to 150° C. Suitable solvents and diluents are, for example, ethers or ethereal compounds, such as diethyl ether, diisopropyl ether, dioxane or tetrahydrofuran; aromatic hydrocarbons, such as benzene, toluene or xylenes; ketones, such as acetone, methyl ethyl ketone or cyclohexanone, alcohols or dimethylformamide. The reaction is either carried out in the presence of a base or the resulting salt is subjected to treatment with a base after the reaction (see J. B. Hendricksen et al., "Organic Chemistry", McGraw Hill Book Co., 1970, p. 378-382).

Process C is advantageously carried out in an aprotic organic solvent or diluent under normal pressure. The temperature is from 0° to +150° C., preferably from +10° to 50° C. Suitable solvents and diluents are, for example, ethers or ethereal compounds, such as diethyl ether, dipropyl ether, dibutyl ether, dioxane, dimethoxyethane or tetrahydrofuran; N,N-dialkylated carboxylic acid amides; aliphatic, aromatic and halogenated hydrocarbons, such as benzene, toluene, xylenes, chloroform, methylene chloride, carbon tetrachloride or chlorobenzene; nitriles, such as acetonitrile or propionitrile; ketones, such as acetone, methyl ethyl ketone, methyl isopropyl ketone or cyclohexanone. The removal of hydrogen sulfide is effected according to procedures described in the literature (T. Shibanuma, Chemistry Letters 1977, p. 575-576; S. Kim, Tetrahedron Letters 1985, p. 1661-1664; W. Weith, B. 6, 1873, p. 1398; G. Amiard, Bull. Soc. chim. 1956, p. 1360). As removal reagents there are used, inter alia, HgO, certain pyridinium salts, chloroacetic acid esters, cyanuric acid chloride, p-toluenesulfochloride or certain phosphoric acid ester derivatives.

The isothiocyanates of formula II can be prepared according to methods known in principle, for example by reacting an aniline of formula V

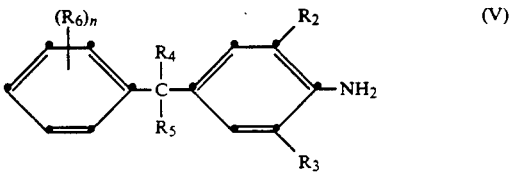

with thiophosgene, $R_2$, $R_3$, $R_4$, $R_5$, $R_6$ and n being as defined for formula I.

The process for the preparation of the compounds of formula II is advantageously carried out under normal pressure and at a temperature of from 0° to +100° C. in the presence of an organic or inorganic base and a solvent or diluent that is inert towards the reactants. Suitable solvents and diluents are, inter alia, ethers or ethereal compounds, such as, for example, diethyl ether, diisopropyl ether, dioxane or tetrahydrofuran; aromatic hydrocarbons, such as, for example, benzene, toluene or xylenes; ketones, such as acetone, methyl ethyl ketone or cyclohexanone; or chlorinated hydrocarbons, such as dichloromethane or tetrachloromethane.

Suitable bases may be of organic or inorganic origin, such as, for example, sodium hydride, sodium or calcium carbonate, tertiary amines, such as triethylamine, triethylenediamine or 4-dimethylaminopyridine or pyridine.

It is also possible to prepare the isothiocyanates of formula II via the corresponding thiourea that is unsubstituted at one N atom. An aniline of formula V is reacted with ammonium thiocyanate in acidic medium, preferably in a medium containing a mineral acid, to form the corresponding thiourea which, for its part, splits off ammonia on heating to from +130° to 200° C. and is converted into an isothiocyanate of formula II (see Saul Patai "The chemistry of cyanates and their thio derivatives", John Wiley and Sons, 1977, p. 1032 ff; Chemistry and Industry, Jul. 3, 1954, p. 735; J. N. Baxter et al., "New method of preparation of aryl isothiocyanates").

The anilines of formula V can for their part be prepared according to methods known in principle, for example by reacting an aniline of formula VI

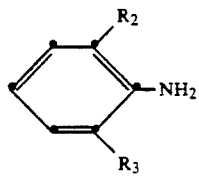

(VI)

at elevated temperature and, if desired, under pressure in the presence of an acid acting as catalyst, preferably a metal salt, such as, for example, zinc chloride in aqueous acidic medium, with a compound of formula VII

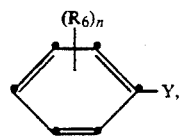

(VII)

(see EP-OS 069 065).

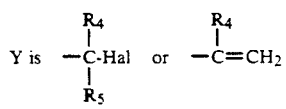

in which Hal is halogen, especially chlorine, and $R_4$, $R_5$, $R_6$ and n are as defined for formula I. Another possible preparation method is to react an aniline of formula Va–Vc

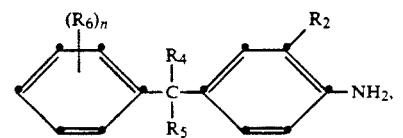

(Va)

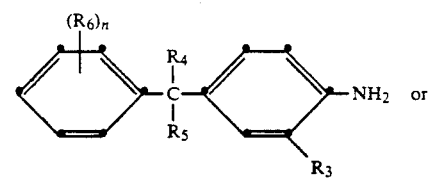

(Vb)

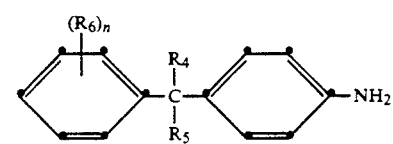

(Vc)

with an alkene or cycloalkene corresponding to $R_2$ or $R_3$ in the presence of aluminium and aluminium chloride under pressure and at elevated temperature (see DE-OS 27 27 529).

Anilines of formula V in which $R_2$ and/or $R_3$ are(is) $C_5$–$C_6$cycloalkenyl can be prepared in accordance with the Aza-Claisen rearrangement (see I. B. Abdrakhmanov et al., Zh. Org. Khim. 15, 2601, 1979; Izv. Akad. Nauk. SSSR, Ser. Khim. 1982, 2160). The catalytic hydrogenation of these anilines yields anilines in which $R_2$ and/or $R_3$ are(is) $C_5$–$C_6$cycloalkyl.

Another method that is practicable in many cases is the rearrangement of correspondingly substituted benzylanilines analogously to the method described by M. Elliott et al., J. Chem. Soc. (C) 1967, 1780.

The compounds of formulae II and V are in some cases known or can be prepared according to methods known in principle. The present invention also relates to the novel compounds which correspond to the formulae II' and V'

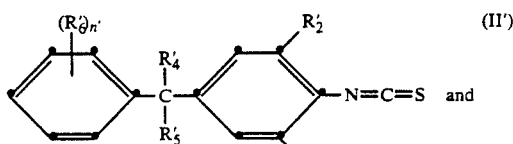

(II')

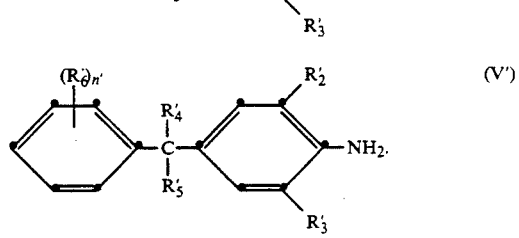

(V')

In these formulae, each of $R_2'$ and $R_3'$ is is $C_3$–$C_5$alkyl or $C_5$–$C_6$cycloalkyl, especially $C_3$–$C_5$alkyl; each of $R_4'$ and $R_5'$ is hydrogen or methyl; $R_6'$ is fluorine, chlorine or methyl; and n' is 0 or 1, especially 0.

The compounds of formulae III, IV, VI and VII are known or can be prepared according to methods known in principle. Known from EP-OS 175 649 are phenoxyphenylcarbodiimides and, from DE-OS 30 34 905 and EP-OS 025 010, phenoxyphenylthioureas and phenoxyphenylisothioureas having insecticidal and acaricidal action.

Surprisingly it has been found that the compounds of formula I according to the invention are valuable active ingredients in the control of pests while being well tolerated by warm-blooded animals and by plants. The compounds of formula I are therefore suitable, for example, for controlling pests in and on animals and plants. Such pests belong chiefly to the strain of arthropods, such as, especially, insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, such as, for example, mites and ticks. It is possible to control every stage of development of the pests, that is to say the adults, pupae and nymphs as well as, especially, the larvae and eggs. It is possible, especially, to control effectively the larvae and eggs of phytopathogenic insect and mite pests in crops of ornamental and useful plants, such as, for example, in fruit and vegetables. If the compounds of formula I are ingested by imagines, their action can manifest itself in the immediate death of the pests or in reduced oviposition and/or hatching rates. The latter phenomenon is to be observed especially in Coleoptera. In the control of pests that parasiticise animals, especially domestic animals and productive livestock, there come into consideration especially ectoparasites, such as, for example, mites and ticks, and Diptera, such as, for example, Lucilia sericata.

The good pesticidal activity of the compounds of formula I according to the invention corresponds to a mortality of at least 50-60% of the mentioned pests.

The activity of the compounds of the invention or the compositions containing them can be substantially broadened and adapted to the prevailing circumstances by adding other insecticides and/or acaricides. Suitable additives are, for example, representatives of the following classes of active ingredient: organo-phosphorus compounds, nitrophenols and derivatives thereof, formamidines, ureas, carbamates, pyrethroids, chlorinated hydrocarbons and Bacillus thuringiensis preparations.

The compounds of formula I are used in unmodified form, or preferably, together with the inert adjuvants, tolerated by plants, that are conventionally employed in the art of formulation, and can therefore be formulated in known manner, for example, to emulsifiable concentrates, directly sprayable or dilutable solutions, dilute emulsions, wettable powders, soluble powders, dusts, granulates, and also encapsulations in, e.g., polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, for example by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable nonsorbent carriers are materials such as calcite or sand. In addition a great number of granulated materials of inorganic or organic nature can be used, e.g. especially dolomite or pulverised plant residues.

Depending on the nature of the compound of formula I to be formulated or on the nature of the combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also watersoluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Other suitable surfactants that may be mentioned are fatty acid methyltaurin salts, and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, for example the sodium or calcium salt of lignosulfonic acid, of dodecyl sulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described, inter alia, in the following publications:

"McCutcheon's Detergents and Emulsifiers Annual", MC Publishing Corp., Ridgewood, N.J., 1979;

Dr. Helmut Stache, "Tensid Taschenbuch" Carl Hanser Veriag, Munich/Vienna 1981.

The pesticidal compositions usually contain 0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ diluted formulations containing considerably lower concentrations of active ingredient.

The compositions may also contain further auxiliaries, such as stabilisers, antifoams, viscosity regulators, binders and tackifiers, as well as fertilisers or other active ingredients in order to obtain special effects.

EXAMPLE 1

Preparation 1.1. Intermediates 1.1.1. Benzylanilines 1.1.1.1. 2,6-diethyl-4-benzylaniline 74.6 g of diethylaniline are mixed at room temperature with 63.3 g of benzyl chloride and heated for 17 hours at +230° C. (bath temperature). After cooling, the reaction mixture is stirred with 10% aqueous sodium hydroxide and ether. The ether phase is washed twice with water and once with saturated aqueous sodium chloride solution, dried over sodium sulfate and concentrated by evaporation in vacuo. The residue is fractionated in vacuo to give the title compound of formula (Comp. no. 1.1.1.1.)

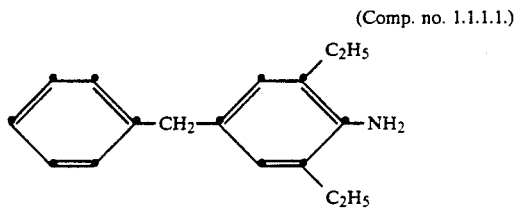

in the form of a colourless oil; b.p. 113°–120° C./0.03 torr; refractive index $n_D^{22}$: 1.5858.

1.1.1.2. 2,6-di-sec-butyl-4-benzylaniline 81 g of 4-benzylaniline, 1.2 g of aluminium powder, 3.6 g of anhydrous aluminium chloride and 100 g of but-1-ene are heated for 24 hours at +260° C. in an autoclave. After cooling, the reaction mass is poured into ice-cold dilute sodium hydroxide solution and taken up in ether. The ether phase is separated off, dried over sodium sulfate and subjected to fractional distillation; b.p. 130°–134° C./0.03 torr. Chromatographic purification on silica gel using hexane/ethyl acetate as eluant affords the title compound of formula (Comp. no. 1.1.1.2.)

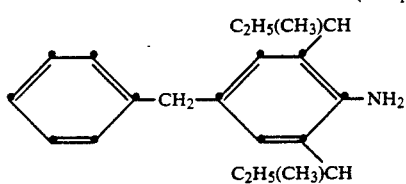

in the form of a colourless oil; refractive index $n_D^{24}$: 1.5579.

The following compounds are prepared in a manner analogous to that described under 1.1.1.1. and 1.1.1.2.:

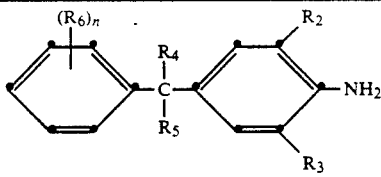

| Comp. no. | $R_2$ | $R_3$ | $R_4$ | $R_5$ | $R_6$ | n | phys. data |
|---|---|---|---|---|---|---|---|
| 1.1.1.3. | $C_2H_5$ | $C_2H_5$ | $CH_3$ | $CH_3$ | — | 0 | $n_D^{24}$: 1.5750 |
| 1.1.1.4. | $CH(CH_3)_2$ | $CH(CH_3)_2$ | H | H | — | 0 | $n_D^{24}$: 1.5686 |
| 1.1.1.5. | $CH(CH_3)_2$ | $CH(CH_3)_2$ | $CH_3$ | $CH_3$ | — | 0 | $n_D^{22}$: 1.5600 |
| 1.1.1.6. | $CH(CH_3)_2$ | $CH(CH_3)_2$ | $CH_3$ | H | — | 0 | $n_D^{23}$: 1.5636 |
| 1.1.1.7. | $C_2H_5$ | $CH(CH_3)_2$ | H | H | — | 0 | $n_D^{24}$: 1.5762 |
| 1.1.1.8. | $C_2H_5$ | $CH(CH_3)_2$ | H | H | 4-F | 1 | $n_D^{22}$: 1.5636 |
| 1.1.1.9. | $CH(CH_3)_2$ | $CH(CH_3)_2$ | H | H | 4-F | 1 | $n_D^{25}$: 1.5562 |
| 1.1.1.10. | $CH(CH_3)_2$ | $CH(CH_3)_2$ | H | H | 3-F | 1 | $n_D^{24}$: 1.5565 |
| 1.1.1.11. | $CH(CH_3)_2$ | $CH(CH_3)_2$ | H | H | 2-F | 1 | m.p. 38–39° C. |
|  | $CH(CH_3)_2$ | $CH(CH_3)_2$ | H | H | 2,4-$F_2$ | 2 |  |
|  | $CH(CH_3)_2$ | $CH(CH_3)_2$ | H | H | 4-Cl | 1 |  |
|  | $CH(CH_3)_2$ | $CH(CH_3)_2$ | H | H | 2,4-$Cl_2$ | 2 |  |
|  | $CH(CH_3)_2$ | Cyclopentyl | H | H | H | 0 |  |
|  | Cyclopentyl | Cyclopentyl | H | H | H | 0 |  |

1.1.2. Isothiocyanates 1.1.2.1. 2,6-diethyl-4-benzylphenyl isothiocyanate 34.0 g of thiophosgene, 54.8 g of calcium carbonate and 460 ml of dichloromethane are stirred with 230 ml of water. A solution of 59.3 g of 2,6-diethyl-4-benzylaniline in 200 ml of dichloroethane is stirred dropwise into this mixture at room temperature. The reaction mixture is stirred for 2 hours under reflux and, after cooling, is filtered over diatomaceous earth. The organic phase is separated from the filtrate, dried over sodium sulfate and freed of the solvent to give the title compound of formula (Comp. no. 1.1.2.1.)

in the form of a yellow oil which is used without further purification for the next reaction.

The following compounds are prepared in analogous manner.

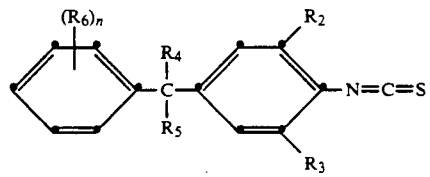

| Comp. no. | R$_2$ | R$_3$ | R$_4$ | R$_5$ | R$_6$ | n | phys. data |
|---|---|---|---|---|---|---|---|
| 1.1.2.3. | C$_2$H$_5$ | C$_2$H$_5$ | CH$_3$ | CH$_3$ | — | 0 | n$_D^{24}$: 1.6101 |
| 1.1.2.4. | CH(CH$_3$)$_2$ | CH(CH$_3$)$_2$ | H | H | — | 0 | Smp. 40–43° C. |
| 1.1.2.5. | CH(CH$_3$)$_2$ | CH(CH$_3$)$_2$ | CH$_3$ | CH$_3$ | — | 0 | n$_D^{27}$: 1.5923 |
| 1.1.2.6. | CH(CH$_3$)$_2$ | CH(CH$_3$)$_2$ | CH$_3$ | H | — | 0 | n$_D^{24}$: 1.5998 |
| 1.1.2.7. | C$_2$H$_5$ | CH(CH$_3$)$_2$ | H | H | — | 0 | n$_D^{23}$: 1.6143 |
| 1.1.1.8. | C$_2$H$_5$ | CH(CH$_3$)$_2$ | H | H | 4-F | 1 | n$_D^{25}$: 1.6023 |
| 1.1.1.9. | CH(CH$_3$)$_2$ | CH(CH$_3$)$_2$ | H | H | 4-F | 1 | n$_D^{24}$: 1.5948 |
| 1.1.1.10. | CH(CH$_3$)$_2$ | CH(CH$_3$)$_2$ | H | H | 3-F | 1 | n$_D^{24}$: 1.5943 |
| 1.1.1.11. | CH(CH$_3$)$_2$ | CH(CH$_3$)$_2$ | H | H | 2-F | 1 | n$_D^{24.5}$: 1.5944 |
| | CH(CH$_3$)$_2$ | CH(CH$_3$)$_2$ | H | H | 2,4-F$_2$ | 2 | |
| | CH(CH$_3$)$_2$ | CH(CH$_3$)$_2$ | H | H | 4-Cl | 1 | |
| | CH(CH$_3$)$_2$ | CH(CH$_3$)$_2$ | H | H | 2,4-Cl$_2$ | 2 | |
| | CH(CH$_3$)$_2$ | Cyclopentyl | H | H | H | 0 | |
| | Cyclopentyl | Cyclopentyl | H | H | H | 0 | |

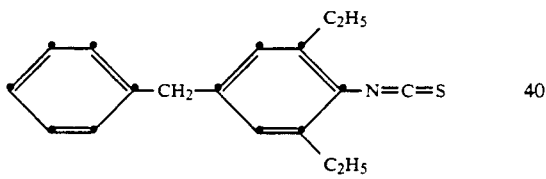

40 in the form of a yellow oil which is used without further purification for the next reaction.

1.1.2.2. 2,6-di-sec-butyl-4-benzylphenyl isothiocyanate 14.3 g of thiophosgene, 23.0 g of calcium carbonate and 460 ml of dichloromethane are stirred with 230 ml of water. A solution of 30.8 g of 2,6-di-sec-butyl-4-benzylaniline in 200 ml of dichloroethane is stirred dropwise into this mixture at room temperature. The reaction mixture is stirred for two hours under reflux and, after cooling, is filtered over diatomaceous earth. The organic phase is separated from the filtrate, dried over sodium sulfate and freed of the solvent to give the title compound of formula (Comp. no. 1.1.2.2.)

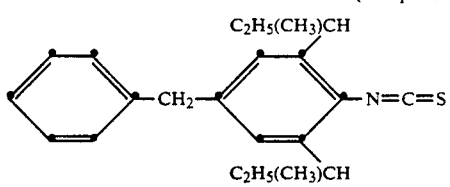

1.2. End products 1.2.1. Phenylthioureas 1.2.1.1.
N-[(2,6-diethyl-4-benzyl)-phenyl]-N'-tert-butylthiourea 22.9 g of 2,6-diethyl-4-benzylphenyl isothiocyanate and 15 g of tert-butylamine are diluted with 100 ml of tetrahydrofuran and left to stand at room temperature for 24 hours. The reaction mixture is poured onto ice-water, the resulting precipitate is filtered off, washed with water and, after being dried, is recrystallised from ethanol to give the title compound of formula (Comp. no. 1.2.1.1.)

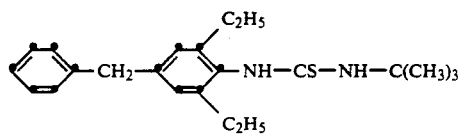

in the form of a colourless solid; m.p. 136°–138° C.

The following compounds are obtained in an analogous manner:

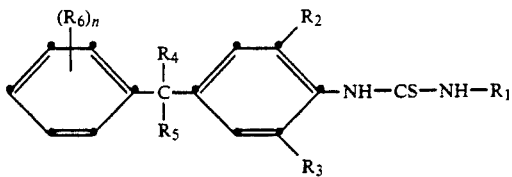

| Comp. no. | R₁ | R₂ | R₃ | R₄ | R₅ | R₆ | n | phys. data |
|---|---|---|---|---|---|---|---|---|
| 1.2.1.2. | $CH(CH_3)_2$ | $C_2H_5$ | $C_2H_5$ | H | H | — | 0 | m.p. 135–137° C. |
| 1.2.1.3. | Cyclopentyl | $C_2H_5$ | $C_2H_5$ | H | H | — | 0 | m.p. 127–129° C. |
| 1.2.1.4. | $C(CH_3)_3$ | $CH(CH_3)_2$ | $CH(CH_3)_2$ | H | H | — | 0 | m.p. 153–154° C. |
| 1.2.1.5. | $C(CH_3)_3$ | $C_2H_5$ | $C_2H_5$ | $CH_3$ | $CH_3$ | — | 0 | m.p. 142–144° C. |
| 1.2.1.6. | $CH(CH_3)_2$ | $C_2H_5$ | $C_2H_5$ | $CH_3$ | $CH_3$ | — | 0 | m.p. 156–158° C. |
| 1.2.1.7. | $C(CH_3)_3$ | $CH(CH_3)C_2H_5$ | $CH(CH_3)C_2H_5$ | H | H | — | 0 | m.p. 134–137° C. |
| 1.2.1.8. | $CH(CH_3)_2$ | $CH(CH_3)C_2H_5$ | $CH(CH_3)C_2H_5$ | H | H | — | 0 | m.p. 144–146° C. |
| 1.2.1.9. | Cyclopentyl | $C_2H_5$ | $C_2H_5$ | $CH_3$ | $CH_3$ | — | 0 | m.p. 171–173° C. |
| 1.2.1.10. | $C(CH_3)_3$ | $CH(CH_3)_2$ | $CH(CH_3)_2$ | $CH_3$ | $CH_3$ | — | 0 | m.p. 144–146° C. |
| 1.2.1.11. | $C(CH_3)_3$ | $C_2H_5$ | $CH(CH_3)_2$ | H | H | — | 0 | m.p. 140–141.5° C. |
| 1.2.1.12. | $CH(CH_3)_2$ | $CH(CH_3)_2$ | $CH(CH_3)_2$ | H | H | — | 0 | m.p. 188–191° C. |
| 1.2.1.13. | Cyclopentyl | $CH(CH_3)_2$ | $CH(CH_3)_2$ | H | H | — | 0 | m.p. 178–180.5° C. |
| 1.2.1.14. | $CH(CH_3)_2$ | $CH(CH_3)_2$ | $CH(CH_3)_2$ | $CH_3$ | H | — | 0 | m.p. 171–173° C. |
| 1.2.1.15. | $C(CH_3)_3$ | $CH(CH_3)_2$ | $CH(CH_3)_2$ | $CH_3$ | H | — | 0 | m.p. 154–155.5° C. |
| 1.2.1.16. | $CH(CH_3)C_2H_5$ | $CH(CH_3)_2$ | $CH(CH_3)_2$ | H | H | — | 0 | m.p. 157–158.5° C. |
| 1.2.1.17. | $CH(CH_3)CH(CH_3)_2$ | $CH(CH_3)_2$ | $CH(CH_3)_2$ | H | H | — | 0 | m.p. 157–159° C. |
| 1.2.1.18. | $CH(CH_3)_2$ | $C_2H_5$ | $CH(CH_3)_2$ | H | H | 4-F | 1 | m.p. 142–144° C. |
| 1.2.1.19. | $C(CH_3)_3$ | $C_2H_5$ | $CH(CH_3)_2$ | H | H | 4-F | 1 | m.p. 145–146° C. |
| 1.2.1.20. | $C(CH_3)_3$ | $CH(CH_3)_2$ | $CH(CH_3)_2$ | H | H | 2-F | 1 | m.p. 153–154° C. |
| 1.2.1.21. | $CH(CH_3)_2$ | $CH(CH_3)_2$ | $CH(CH_3)_2$ | H | H | 2-F | 1 | m.p. 192–194° C. |
| 1.2.1.22. | $C(CH_3)_3$ | $CH(CH_3)_2$ | $CH(CH_3)_2$ | H | H | 4-F | 1 | m.p. 154.5–156° C. |
| 1.2.1.23. | $CH(CH_3)_2$ | $CH(CH_3)_2$ | $CH(CH_3)_2$ | H | H | 3-F | 1 | m.p. 184–186.5° C. |
| 1.2.1.24. | $C(CH_3)_3$ | $CH(CH_3)_2$ | $CH(CH_3)_2$ | H | H | 3-F | 1 | m.p. 138–139.5° C. |
| 1.2.1.25. | $CH(CH_3)_2$ | $CH(CH_3)_2$ | $CH(CH_3)_2$ | H | H | 2-F | 1 | m.p. 192–194° C. |
| 1.2.1.26. | $C(CH_3)_3$ | $CH(CH_3)_2$ | $CH(CH_3)_2$ | H | H | 2-F | 1 | m.p. 153–154° C. |
|  | $C(CH_3)_3$ | $CH(CH_3)_2$ | $CH(CH_3)_2$ | H | H | 2,4-$F_2$ | 2 |  |
|  | $CH(CH_3)_2$ | $CH(CH_3)_2$ | $CH(CH_3)_2$ | H | H | 2,4-$F_2$ | 2 |  |
|  | $C(CH_3)_3$ | $CH(CH_3)_2$ | $CH(CH_3)_2$ | H | H | 4-Cl | 1 |  |
|  | $CH(CH_3)_2$ | $CH(CH_3)_2$ | $CH(CH_3)_2$ | H | H | 4-Cl | 1 |  |
|  | $C(CH_3)_3$ | $CH(CH_3)_2$ | $CH(CH_3)_2$ | H | H | 2,4-$Cl_2$ | 2 |  |
|  | $CH(CH_3)_2$ | $CH(CH_3)_2$ | $CH(CH_3)_2$ | H | H | 2,4-$Cl_2$ | 2 |  |
|  | $C(CH_3)_3$ | $CH(CH_3)_2$ | Cyclopentyl | H | H | — | 0 |  |
|  | $CH(CH_3)_2$ | $CH(CH_3)_2$ | Cyclopentyl | H | H | — | 0 |  |
|  | $C(CH_3)_3$ | Cyclopentyl | Cyclopentyl | H | H | — | 0 |  |
|  | $CH(CH_3)_2$ | Cyclopentyl | Cyclopentyl | H | H | — | 0 |  |
|  | 1-($CH_3$)-cyclopropyl | $CH(CH_3)_2$ | $CH(CH_3)_2$ | H | H | — | 0 |  |
|  | 1-($CH_3$)-cyclopropyl | $CH(CH_3)_2$ | $CH(CH_3)_2$ | $CH_3$ | H | — | 0 |  |

1.2.2. Phenylisothioureas

1.2.2.1. N-[(2,6-diethyl-4-benzyl)-phenyl]-N'-(tert-butyl-S-methylisothiourea 4.8 g of methyl iodide are added at room temperature to 8 g of N-[(2,6-diethyl-4-benzyl)-phenyl]-N'-tert-butyl-thiourea in 30 ml of ethanol and the batch is heated for 4 hours at +50° C. while stirring. After cooling, the reaction solution is poured onto water and the resulting precipitate, the hydriodide of the isothiourea, is isolated by filtration (m.p. 140°–144° C.). This isothiuronium hydriodide is dissolved in dichloromethane, extracted by shaking twice with 5% aqueous sodium carbonate solution and finally washed neutral with water. The organic phase is dried over sodium sulfate and the solvent is evaporated off to give the title compound of formula (Comp. no. 1.2.2.1.)

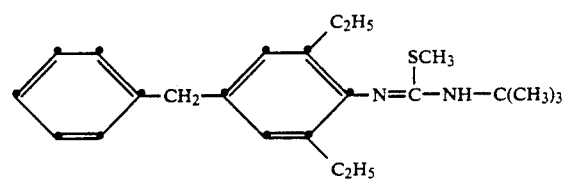

in the form of a colourless crystal powder; m.p. 62.5°–64.5° C.

The following compounds are prepared in an analogous manner:

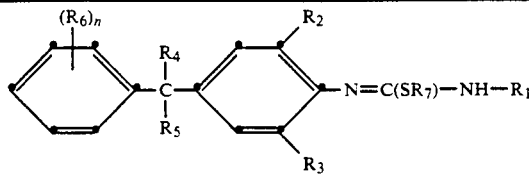

| Comp. no. | R1 | R2 | R3 | R4 | R5 | R6 | R7 | n | phys. data |
|---|---|---|---|---|---|---|---|---|---|
| 1.2.2.2. | $CH(CH_3)_2$ | $C_2H_5$ | $C_2H_5$ | H | H | — | $CH_3$ | 0 | m.p. 69–71° C. |
| 1.2.2.3. | Cyclopentyl | $C_2H_5$ | $C_2H_5$ | H | H | — | $CH_3$ | 0 | m.p. 47–48° C. |
| 1.2.2.4. | $C(CH_3)_3$ | $CH(CH_3)_2$ | $CH(CH_3)_2$ | H | H | — | $CH_3$ | 0 | m.p. 104–105° C. |
| 1.2.2.5. | $C(CH_3)_3$ | $C_2H_5$ | $C_2H_5$ | $CH_3$ | $CH_3$ | — | $CH_3$ | 0 | $n_D^{22}$: 1.5700 |
| 1.2.2.6. | $CH(CH_3)_2$ | $C_2H_5$ | $C_2H_5$ | $CH_3$ | $CH_3$ | — | $CH_3$ | 0 | $n_D^{22}$: 1.5720 |
| 1.2.2.7. | $C(CH_3)_3$ | $CH(CH_3)C_2H_5$ | $CH(CH_3)C_2H_5$ | H | H | — | $CH_3$ | 0 | m.p. 82–85.5° C. |
| 1.2.2.8. | $CH(CH_3)_2$ | $CH(CH_3)C_2H_5$ | $CH(CH_3)C_2H_5$ | H | H | — | $CH_3$ | 0 | m.p. 34–37° C. |
| 1.2.2.9. | Cyclopentyl | $C_2H_5$ | $C_2H_5$ | $CH_3$ | $CH_3$ | — | $CH_3$ | 0 | m.p. 47–48.5° C. |
| 1.2.2.10. | $C(CH_3)_3$ | $CH(CH_3)_2$ | $CH(CH_3)_2$ | $CH_3$ | $CH_3$ | — | $CH_3$ | 0 | m.p. 85–87° C. |
| 1.2.2.11. | $CH(CH_3)_2$ | $CH(CH_3)_2$ | $CH(CH_3)_2$ | H | H | — | $C_2H_5$ | 0 | $n_D^{26}$: 1.5592 |
| 1.2.2.12. | $CH(CH_3)_2$ | $CH(CH_3)_2$ | $CH(CH_3)_2$ | H | H | — | $(CH_2)_2CH_3$ | 0 | $n_D^{26}$: 1.5552 |
| 1.2.2.13. | $CH(CH_3)_2$ | $CH(CH_3)_2$ | $CH(CH_3)_2$ | H | H | — | $CH_3$ | 0 | m.p. 73.5–75.5° C. |
| 1.2.2.14. | Cyclopentyl | $CH(CH_3)_2$ | $CH(CH_3)_2$ | H | H | — | $CH_3$ | 0 | m.p. 81.5–83.5° C. |
| 1.2.2.15. | $C(CH_3)_3$ | $C_2H_5$ | $CH(CH_3)_2$ | H | H | — | $CH_3$ | 0 | m.p. 76–78.5° C. |
| 1.2.2.16. | $C(CH_3)_3$ | $C_2H_5$ | $CH(CH_3)_2$ | H | H | — | $C_2H_5$ | 0 | $n_D^{25}$: 1.5639 |
| 1.2.2.17. | $C(CH_3)_3$ | $C_2H_5$ | $CH(CH_3)_2$ | H | H | — | $(CH_2)_2CH_3$ | 0 | $n_D^{25}$: 1.5598 |
| 1.2.2.18. | $C(CH_3)_3$ | $CH(CH_3)_2$ | $CH(CH_3)_2$ | $CH_3$ | H | — | $CH_3$ | 0 | m.p. 106.5–110° C. |
| 1.2.2.19. | $CH(CH_3)_2$ | $CH(CH_3)_2$ | $CH(CH_3)_2$ | $CH_3$ | H | — | $CH_3$ | 0 | m.p. 66–69° C. |
| 1.2.2.20. | $CH(CH_3)C_2H_5$ | $CH(CH_3)_2$ | $CH(CH_3)_2$ | H | H | — | $CH_3$ | 0 | $n_D^{24}$: 1.5616 |
| 1.2.2.21. | $CH(CH_3)C_2H_5$ | $CH(CH_3)_2$ | $CH(CH_3)_2$ | H | H | — | $C_2H_5$ | 0 | $n_D^{24}$: 1.5575 |
| 1.2.2.22. | $C(CH_3)_3$ | $C_2H_5$ | $CH(CH_3)_2$ | H | H | 4-F | $CH_3$ | 1 | m.p. 65–67° C. |
| 1.2.2.23. | $CH(CH_3)C_2H_5$ | $CH(CH_3)_2$ | $CH(CH_3)_2$ | H | H | — | $(CH_2)_2CH_3$ | 0 | $n_D^{24.5}$: 1.5525 |
| 1.2.2.24. | $CH(CH_3)CH(CH_3)_2$ | $CH(CH_3)_2$ | $CH(CH_3)_2$ | H | H | — | $CH_3$ | 0 | m.p. 57.5–60° C. |
| 1.2.2.25. | $CH(CH_3)_2$ | $C_2H_5$ | $CH(CH_3)_2$ | H | H | 4-F | $CH_3$ | 1 | $n_D^{24}$: 1.5620 |
| 1.2.2.26. | $C(CH_3)_3$ | $CH(CH_3)_2$ | $CH(CH_3)_2$ | H | H | 2-F | $CH_3$ | 1 | m.p. 93–96° C. |
| 1.2.2.27. | $C(CH_3)_3$ | $CH(CH_3)_2$ | $CH(CH_3)_2$ | H | H | 3-F | $CH_3$ | | m.p. 72–75° C. |
| 1.2.2.28. | $C(CH_3)_3$ | $CH(CH_3)_2$ | $CH(CH_3)_2$ | H | H | 4-F | $CH_3$ | 1 | m.p. 83–85.5° C. |
| 1.2.2.29. | $CH(CH_3)_2$ | $CH(CH_3)_2$ | $CH(CH_3)_2$ | H | H | 3-F | $CH_3$ | 1 | m.p. 61–62.5° C. |
| 1.2.2.30. | $CH(CH_3)CH(CH_3)_2$ | $CH(CH_3)_2$ | $CH(CH_3)_2$ | H | H | — | $(CH_2)_2CH_3$ | 0 | $n_D^{25}$: 1.5485 |
| 1.2.2.31. | $CH(CH_3)CH(CH_3)_2$ | $CH(CH_3)_2$ | $CH(CH_3)_2$ | H | H | — | $C_2H_5$ | 0 | $n_D^{25}$: 1.5515 |
| 1.2.2.32. | $CH(CH_3)CH(CH_3)_2$ | $CH(CH_3)_2$ | $CH(CH_3)_2$ | H | H | — | $CH_3$ | 0 | HI salt m.p. 190–194° C. |
| 1.2.2.33. | $CH(CH_3)CH(CH_3)_2$ | $CH(CH_3)_2$ | $CH(CH_3)_2$ | H | H | — | $C_2H_5$ | 0 | HI salt m.p. 163–168° C. |
| 1.2.2.34. | $CH(CH_3)CH(CH_3)_2$ | $CH(CH_3)_2$ | $CH(CH_3)_2$ | H | H | — | $(CH_2)_2CH_3$ | 0 | HI salt m.p. 156–159° C. |
| 1.2.2.35. | $C(CH_3)_3$ | $CH(CH_3)_2$ | $CH(CH_3)_2$ | H | H | 3-F | $CH_3$ | 1 | HI salt m.p. 160–163.5° C. |
| | $C(CH_3)_3$ | $CH(CH_3)_2$ | $CH(CH_3)_2$ | H | H | 2,4-$F_2$ | $CH_3$ | 2 | |
| | $CH(CH_3)_2$ | $CH(CH_3)_2$ | $CH(CH_3)_2$ | H | H | 2,4-$F_2$ | $CH_3$ | 2 | |
| | $C(CH_3)_3$ | $CH(CH_3)_2$ | $CH(CH_3)_2$ | H | H | 4-Cl | $CH_3$ | 1 | |
| | $CH(CH_3)_2$ | $CH(CH_3)_2$ | $CH(CH_3)_2$ | H | H | 4-Cl | $CH_3$ | 1 | |
| | $C(CH_3)_3$ | $CH(CH_3)_2$ | $CH(CH_3)_2$ | H | H | 2,4-$Cl_2$ | $CH_3$ | 2 | |
| | $CH(CH_3)_2$ | $CH(CH_3)_2$ | $CH(CH_3)_2$ | H | H | 2,4-$Cl_2$ | $CH_3$ | 2 | |
| | $C(CH_3)_3$ | $CH(CH_3)_2$ | Cyclopentyl | H | H | — | $CH_3$ | 0 | |
| | $CH(CH_3)_2$ | $CH(CH_3)_2$ | Cyclopentyl | H | H | — | $CH_3$ | 0 | |
| | $C(CH_3)_3$ | Cyclopentyl | Cyclopentyl | H | H | — | $CH_3$ | 0 | |
| | $CH(CH_3)_2$ | Cyclopentyl | Cyclopentyl | H | H | — | $CH_3$ | 0 | |
| | 1-($CH_3$)-cyclopropyl | $CH(CH_3)_2$ | $CH(CH_3)_2$ | H | H | — | $CH_3$ | 0 | |
| | 1-($CH_3$)-cyclopropyl | $CH(CH_3)_2$ | $CH(CH_3)_2$ | $CH_3$ | H | — | $CH_3$ | 0 | |
| | $C(CH_3)_3$ | $CH(CH_3)_2$ | $CH(CH_3)_2$ | H | H | — | $C_2H_5$ | 0 | |
| | $C(CH_3)_3$ | $CH(CH_3)_2$ | $CH(CH_3)_2$ | H | H | — | $(CH_2)_2CH_3$ | 0 | |
| | $C(CH_3)_3$ | $CH(CH_3)_2$ | $CH(CH_3)_2$ | H | H | — | $(CH_2)_3CH_3$ | 0 | |
| | $C(CH_3)_3$ | $CH(CH_3)_2$ | $CH(CH_3)_2$ | H | H | — | $CH_2CH=CH_2$ | 0 | |
| | $CH(CH_3)_2$ | $CH(CH_3)_2$ | $CH(CH_3)_2$ | H | H | — | $(CH_2)_3CH_3$ | 0 | |
| | $CH(CH_3)_2$ | $CH(CH_3)_2$ | $CH(CH_3)_2$ | H | H | — | $CH_2CH=CH_2$ | 0 | |
| | $CH(CH_3)_2$ | $C_2H_5$ | $CH(CH_3)_2$ | H | H | — | $CH_3$ | 0 | |
| | $CH(CH_3)_2$ | $CH(CH_3)_2$ | Cyclopentyl | H | H | — | $CH_3$ | 0 | |

1.2.3. Phenylcarbodiimides

1.2.3.1. N-[(2,6-diethyl-4-benzyl)phenyl]-N'-tert-butylcarbodiimide 8 g of N-[(2,6-diethyl-4-benzyl)-phenyl]-N'-tert-butylthiourea and 6.9 g of 2-chloro-1-methylpyridinium iodide are placed in 30 ml of dry acetonitrile and, at room temperature, 5.5 g of triethylamine in 20 ml of acetonitrile are added dropwise thereto and the batch is stirred for 3 hours under reflux. The solvent is then removed in vacuo and the residue is taken up in hexane and filtered. The filtrate is washed three times with water, dried over sodium sulfate, decolorised with silica gel and freed of the solvent in vacuo to give the title compound of formula (Comp. no. 1.2.3.1.)

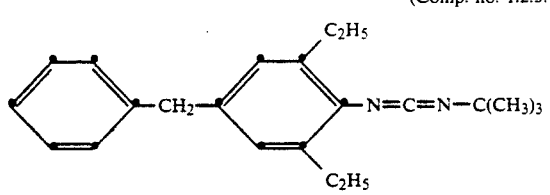

in the form of a colourless oil; refractive index $n_D^{22}$: 1.5658.

The following compounds are prepared in an analogous manner:

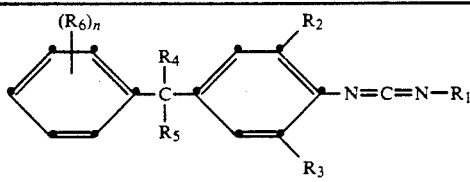

| Comp. no. | $R_1$ | $R_2$ | $R_3$ | $R_4$ | $R_5$ | $R_6$ | n | phys. data |
|---|---|---|---|---|---|---|---|---|
| 1.2.3.2. | $CH(CH_3)_2$ | $C_2H_5$ | $C_2H_5$ | H | H | — | 0 | $n_D^{22}$: 1.5731 |
| 1.2.3.3. | Cyclopentyl | $C_2H_5$ | $C_2H_5$ | H | H | — | 0 | $n_D^{22}$: 1.5839 |
| 1.2.3.4. | $C(CH_3)_3$ | $CH(CH_3)_2$ | $CH(CH_3)_2$ | H | H | — | 0 | $n_D^{22}$: 1.5552 |
| 1.2.3.5. | $C(CH_3)_3$ | $C_2H_5$ | $C_2H_5$ | $CH_3$ | $CH_3$ | — | 0 | $n_D^{23}$: 1.5609 |
| 1.2.3.6. | $CH(CH_3)_2$ | $C_2H_5$ | $C_2H_5$ | $CH_3$ | $CH_3$ | — | 0 | $n_D^{24}$: 1.5657 |
| 1.2.3.7. | $C(CH_3)_3$ | $CH(CH_3)C_2H_5$ | $CH(CH_3)C_2H_5$ | H | H | — | 0 | $n_D^{26}$: 1.5460 |
| 1.2.3.8. | $CH(CH_3)_2$ | $CH(CH_3)C_2H_5$ | $CH(CH_3)C_2H_5$ | H | H | — | 0 | $n_D^{26}$: 1.5495 |
| 1.2.3.9. | Cyclopentyl | $C_2H_5$ | $C_2H_5$ | $CH_3$ | $CH_3$ | — | 0 | $n_D^{24}$: 1.5772 |
| 1.2.3.10. | $C(CH_3)_3$ | $CH(CH_3)_2$ | $CH(CH_3)_2$ | $CH_3$ | $CH_3$ | — | 0 | $n_D^{25}$: 1.5472 |
| 1.2.3.11. | $C(CH_3)_3$ | $C_2H_5$ | $CH(CH_3)_2$ | H | H | — | 0 | $n_D^{25}$: 1.5588 |
| 1.2.3.12. | $CH(CH_3)_2$ | $CH(CH_3)_2$ | $CH(CH_3)_2$ | H | H | — | 0 | $n_D^{26}$: 1.5593 |
| 1.2.3.13. | Cyclopentyl | $CH(CH_3)_2$ | $CH(CH_3)_2$ | H | H | — | 0 | $n_D^{26}$: 1.5704 |
| 1.2.3.14. | $CH(CH_3)_2$ | $CH(CH_3)_2$ | $CH(CH_3)_2$ | $CH_3$ | H | — | 0 | $n_D^{23}$: 1.5562 |
| 1.2.3.15. | $C(CH_3)_3$ | $CH(CH_3)_2$ | $CH(CH_3)_2$ | $CH_3$ | H | — | 0 | $n_D^{23}$: 1.5516 |
| 1.2.3.16. | $CH(CH_3)C_2H_5$ | $CH(CH_3)_2$ | $CH(CH_3)_2$ | H | H | — | 0 | $n_D^{25.5}$: 1.5559 |
| 1.2.3.17. | $CH(CH_3)CH(CH_3)_2$ | $CH(CH_3)_2$ | $CH(CH_3)_2$ | H | H | — | 0 | $n_D^{25.5}$: 1.5538 |
| 1.2.3.18. | $CH(CH_3)_2$ | $C_2H_5$ | $CH(CH_3)_2$ | H | H | 4-F | 1 | $n_D^{24}$: 1.5555 |
| 1.2.3.19. | $C(CH_3)_3$ | $CH(CH_3)_2$ | $CH(CH_3)_2$ | H | H | 2-F | 1 | $n_D^{25}$: 1.5458 |
| 1.2.3.20. | $C(CH_3)_3$ | $C_2H_5$ | $CH(CH_3)_2$ | H | H | 4-F | 1 | $n_D^{23}$: 1.5505 |
| 1.2.3.21. | $C(CH_3)_3$ | $CH(CH_3)_2$ | $CH(CH_3)_2$ | H | H | 4-F | 1 | $n_D^{24}$: 1.5445 |
| 1.2.3.22. | $CH(CH_3)_2$ | $CH(CH_3)_2$ | $CH(CH_3)_2$ | H | H | 3-F | 1 | $n_D^{23}$: 1.5483 |
| 1.2.3.23. | $C(CH_3)_3$ | $CH(CH_3)_2$ | $CH(CH_3)_2$ | H | H | 3-F | 1 | $n_D^{22}$: 1.5458 |
|  | $CH(CH_3)_2$ | $CH(CH_3)_2$ | $CH(CH_3)_2$ | H | H | 2-F | 1 |  |
|  | $C(CH_3)_3$ | $CH(CH_3)_2$ | $CH(CH_3)_2$ | H | H | 2,4-$F_2$ | 2 |  |
|  | $CH(CH_3)_2$ | $CH(CH_3)_2$ | $CH(CH_3)_2$ | H | H | 2,4-$F_2$ | 2 |  |
|  | $C(CH_3)_3$ | $CH(CH_3)_2$ | $CH(CH_3)_2$ | H | H | 4-Cl | 1 |  |
|  | $CH(CH_3)_2$ | $CH(CH_3)_2$ | $CH(CH_3)_2$ | H | H | 4-Cl | 1 |  |
|  | $C(CH_3)_3$ | $CH(CH_3)_2$ | $CH(CH_3)_2$ | H | H | 2,4-$Cl_2$ | 2 |  |
|  | $CH(CH_3)_2$ | $CH(CH_3)_2$ | $CH(CH_3)_2$ | H | H | 2,4-$Cl_2$ | 2 |  |
|  | $C(CH_3)_3$ | $CH(CH_3)_2$ | Cyclopentyl | H | H | — | 0 |  |
|  | $CH(CH_3)_2$ | $CH(CH_3)_2$ | Cyclopentyl | H | H | — | 0 |  |
|  | $C(CH_3)_3$ | Cyclopentyl | Cyclopentyl | H | H | — | 0 |  |
|  | $CH(CH_3)_2$ | Cyclopentyl | Cyclopentyl | H | H | — | 0 |  |
|  | 1-($CH_3$)-Cyclopropyl | $CH(CH_3)_2$ | $CH(CH_3)_2$ | H | H | — | 0 |  |
|  | 1-($CH_3$)-Cyclopropyl | $CH(CH_3)_2$ | $CH(CH_3)_2$ | $CH_3$ | H | — | 0 |  |

EXAMPLE 2

Formulations of Active Ingredients of Formula I According to Preparation Examples 1.2. (throughout percentages are by weight)

| 2.1. Emulsifiable concentrates | a) | b) |
|---|---|---|
| compound according to Preparation Examples 1.2. | 10% | 25% |
| calcium dodecylbenzenesulfonate | — | 5% |
| castor oil polyethylene glycol ether (36 moles of ethylene oxide) | 25% | 5% |
| cyclohexanone | — | 40% |
| butanol | 15% | — |
| xylene mixture | — | 25% |
| ethyl acetate | 50% | — |

Emulsions of any desired concentration can be produced from such concentrates by dilution with water.

| 2.2. Solutions | a) | b) |
|---|---|---|
| compound according to Preparation Examples 1.2. | 10% | 5% |
| polyethylene glycol (mol. wt. 400) | 70% | — |
| N-methyl-2-pyrrolidone | 20% | 20% |
| epoxidised coconut oil | — | 1% |
| petroleum fraction (boiling range 160–190° C.) | — | 74% |

These solutions are suitable for application in the form of microdrops.

| 2.3. Granulates | a) | b) |
|---|---|---|
| compound according to Preparation | 5% | 10% |

-continued

| 2.3. Granulates | a) | b) |
|---|---|---|
| Examples 1.2. | | |
| kaolin | 94% | — |
| highly dispersed silicic acid | 1% | — |
| attapulgite | — | 90% |

The active ingredient is dissolved in methylene chloride, the solution is sprayed onto the carrier and the solvent is subsequently evaporated off in vacuo.

| 2.4. Extruder granulate | |
|---|---|
| compound according to Preparation Examples 1.2. | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.5. Coated granulate | |
|---|---|
| compound according to Preparation Examples 1.2. | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | a) | b) | c) | d) |
|---|---|---|---|---|
| compound according to Preparation Examples 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and optionally grinding the mixture in a suitable mill.

| 2.7. Wettable powders | a) | b) | c) |
|---|---|---|---|
| compound according to Preparation Examples 1.2. | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is ground in a suitable mill, affording wettable powders which can be diluted with water to give suspensions of any desired concentration.

| 2.8. Suspension concentrate | |
|---|---|
| compound according to Preparation | 40% |

| 2.8. Suspension concentrate | |
|---|---|
| Examples 1.2. | |
| ethylene glycol | 10% |
| nonylphenolpolyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Tests 3.1. Action against *Musca domestica*

A sugar cube is so moistened with a solution of the test compound that the concentration of active ingredient in the cube after drying is 500 ppm. The treated cube is placed on a dish together with a wet cotton wool swab and covered with a beaker. 10 adult one-week-old, OP-resistant flies are placed under the beaker and kept at 25° C. and 50% humidity. The insecticidal action is determined after 24 hours by evaluating the mortality rate.

Compounds according to Examples 1.2. exhibit good activity in this test.

3.2. Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

Compounds according to Examples 1.2. exhibit good activity against *Lucilia sericata* in this test.

3.3. Action against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker. Mortality counts are made after 2 and 7 days.

Compounds according to Examples 1.2. exhibit good activity in this test.

3.4. Action against ticks in various stages of development 10 fresh Boophilus microplus females fully replete with blood are affixed in a row in the dorsal position to a PVC plate and covered with a cotton wool swab. 10 ml of the aqueous test solution are then poured over the test organisms. One hour later the cotton wool swab is removed and the ticks are dried overnight at 24° C. After drying, the ticks are kept at 28° C. and 80% humidity for 4 weeks until oviposition has taken place and the larvae have started to hatch.

Each test compound is tested in a concentration of 500 ppm. The acaricidal action manifests itself in the females as mortality or sterility or in the egg deposits as the blocking of embryogenesis or the act of hatching. All the compounds are tested against two different strains of tick, the OP-resistant BIARRA strain and the amidine-resistant ULAM strain.

Compounds according to Examples 1.2. exhibit good activity in this test.

3.5. Stomach poison action against *Spodoptera littoralis* larvae ($L_1$)

Cotton plants in the cotyledon stage are sprayed with an aqueous emulsion (obtained from a 10% emulsifiable concentrate) containing 400 ppm of the test compound.

After the coating has dried, each cotton plant is populated with *Spodoptera littoralis* larvae in the first larval stage. The test is carried out at 26° C. and about 50% relative humidity. Mortality is assessed after 2 and 3 days, and defects in the development and sloughing of the developed larvae are assessed after 5 days.

Compounds according to Examples 1.2. exhibit good activity in this test.

3.6. Stomach poison action against *Spodoptera littoralis* and *Heliothis virescens* larvae ($L_3$)

Potted soybean plants (pot size: 10 cm diameter) in the 4-leaf stage are sprayed with aqueous emulsions containing the test compound in a concentration of 400 ppm.

After 2 days each treated soybean plant is populated with 10 larvae of *Spodoptera littoralis* and 10 larvae of *Heliothis virescens* in the third larval stage. The test is carried out at 26° C. and about 60% relative humidity in dim light. After 2 and 5 days evaluation is made to determine the percentage mortality of the larvae.

Compounds according to Examples 1.2. are 80-100% effective (mortality).

3.7. Stomach poison action against *Plutella xylostella* and *Crocidolomia binotalis* larvae ($L_2$)

Potted Chinese cabbage plants (pot size: 10 cm diameter) in the 4-leaf stage are sprayed with aqueous emulsions containing the test compound in a concentration of 400 ppm.

After 2 days, each treated Chinese cabbage plant is populated with 10 *Plutella xylostella* or *Crocidolomia binotalis* larvae in the $L_2$ stage. The test is carried out at 26° C. and about 60% relative humidity in dim light. After 2 and 5 days evaluation is made to determine the percentage mortality of the larvae.

Compounds according to Examples 1.2. are 80-100% effective (mortality).

3.8. Contact action against *Nilaparvata lugens* (nymphs)

The test is carried out with growing plants. For this purpose rice plants about 20 days old and about 15 cm in height are planted into pots (diameter 5.5 cm).

The plants are each sprayed on a rotary table with 40 ml of an acetonic solution containing 400 ppm of the test compound. After the spray-coating has dried, each plant is populated with 20 nymphs of the test organisms in the second or third stage. In order to prevent the cicadas from escaping, a plexiglass cylinder is slipped over each of the populated plants and sealed with a gauze top. The nymphs are kept for 6 days on the treated plants which have to be resprayed at least once. The test is carried out at a temperature of about 23° C. and at 55% relative humidity and the plants are exposed to light for a period of 16 hours per day.

Compounds according to Examples 1.2. exhibit good activity in this test.

3.9. Systemic action against *Nilaparvata lugens*

Rice plants about 10 days old (about 10 cm in height) are each placed in a plastic beaker which contains 20 ml of an aqueous emulsion formulation of the test compound in a concentration of 100 ppm and which is closed by a perforated plastic lid. The root of each rice plant is pushed through a hole in the plastic lid into the aqueous test formulation. The hole is sealed with cotton wool to fix the plant and to exclude the effect of the gas phase from the test formulation. Each rice plant is then populated with 20 nymphs of *Nilaparvata lugens* in the $N_2$ to $N_3$ stage and is covered with a plastic cylinder. The test is carried out at 26° C. and about 60% relative humidity and the plants are exposed to light for a period of 16 hours per day. After 2 and 5 days a count is made of the number of test organisms killed in comparison with untreated controls, thereby establishing whether the test compound absorbed via the roots kills the test organisms on the upper parts of the plants.

Compounds according to Examples 1.2. are 80-100% effective (mortality) against *Nilaparvata lugens* in this test.

3.10. Action against plant-destructive acarids: *Tetranychus cinnabarinus* (OP-resistant)

24 hours before the test for acaricidal action, the primary leaves of *Phaseolus vulgaris* plants are infected with an infested piece of leaf from a mass culture of *Tetranychus cinnabarinus* (the resistance refers to the tolerance to diazinone).

The treated infested plants are sprayed to drip point with a test solution containing 200 ppm of the respective test compound. A count of the number of living and dead imagines and larvae (all mobile stages) is made under a stereoscopic microscope after 48 hours and again after 7 days. One plant is used for each test compound at its given concentration and for each test species. During the test run, the plants are kept in greenhouse compartments at 25° C.

Compounds according to Examples 1.2. exhibit good activity against *Tetranychus cinnabarinus* in this test.

3.11. Ovicidal action against *Tetranychus cinnabarinus* (OP-resistant)

Potted phaseolus vulgaris plants in the primary leaf stage are each populated twice with 30 females of *Tetranychus cinnabarinus*. After oviposition for 24 hours, the females are removed from the plants with a suction pump (water-jet pump), so that only the egg deposits remain on the plants.

The egg-infested plants are then sprayed to drip point with an aqueous emulsion containing 200 ppm of the test compound and kept for 5 days at 25° C. and about 50% relative humidity. After this time a count is made to determine the percentage mortality of the eggs and of hatched larvae.

Compounds according to Examples 1.2. exhibit good activity in this test.

3.12. Miticidal leaf penetration action against *Tetranychus cinnabarinus*

Potted dwarf bean plants in the primary leaf stage infested with *Tetranychus cinnabarinus* are used for the test. The plants are populated with the mites one day before the application of the test compound.

The upper sides of the leaves of the test plants infested with these mites are sprayed with an emulsion formulation containing 400 ppm of the test compound. When the spray coating has dried, the edge of the upper side of each of a number of infested leaves is defined with a line of viscous glue [Raupenleim (anti-caterpillar glue)] in order to prevent the mites on the underside of the leaf from passing onto the upper side.

The treated plants are then kept in a greenhouse at a temperature of 25° C. to 27° C. and at a relative humidity of about 50%. Six days after the application of the test compound, a check is carried out to establish whether there has been any translaminar action, that is to say penetration by the test compound from the upper side to the underside of the leaf, by determining the percentage mortality of the eggs and of the larval and adult stages.

Compounds according to Examples 1.2. exhibit good activity in this test.

3.13. Action against *Panonychus ulmi* (OP- and carbamate-resistant

Apple seedlings having about 20-30 leaves, in pots, are each populated with 60 adult *Panonychus ulmi* females. After 7 days the infested plants are sprayed to drip point with an aqueous emulsion containing 400 ppm of the test compound. The treated plants are then kept in a greenhouse for a further 14 days at 25° C. and about 50% relative humidity.

After this time, the test is evaluated by detaching 20 leaves from each plant, removing the mite population from the detached leaves using a brushing-off device and counting the eggs, post-embryonic stages and adults under a stereoscopic microscope. The percentage reduction in the mite population is evaluated in comparison with untreated controls.

Compounds according to Examples 1.2. exhibit good activity in this test.

3.14. Contact action against *Myzus persicae*

Before the start of the test, pea seedlings (Pisum sativum) about 4-5 days old and raised in water are each populated with about 200 insects of the species *Myzus persicae*. The treated plants are sprayed direct to drip point 24 hours later with an aqueous suspension containing 100 ppm of the test compound. Two plants are used for each test compound. A mortality count is made 3 and 5 days after application. The test is carried out at about 21° C. and about 60% relative humidity.

Compounds according to Examples 1.2. exhibit good activity in this test.

3.15 Action against *Nephotettix cincticeps* (nymphs)

The test is carried out on growing plants. For this purpose rice plants about 20 days old and about 15 cm in height are planted into pots (diameter: 5.5 cm).

The plants are each sprayed on a rotary table with 100 ml of an acetonic solution containing 400 ppm of the test compound. After the spray coating has dried, each plant is populated with 20 nymphs ($N_2$ to $N_3$) of the test organisms. To prevent the cicadas from escaping, a plexiglass cylinder is slipped over each of the plants and sealed with a gauze top. The nymphs are kept for 5 days on the treated plants, which have to be resprayed at least once. The test is carried out at a temperature of about 23° C. and 55% relative humidity. The plants are exposed to light for a period of 16 hours per day.

Compounds according to Examples 1.2. exhibit good activity in this test.

3.16. Action against soil insects (*Diabrotica balteata*)

350 ml of soil (consisting of 95% by volume sand and 5% by volume peat) are mixed with 150 ml of each of a number of aqueous emulsion formulations containing the test compound in a concentration of 400 ppm. Then plastic beakers having an upper diameter of about 10 cm are partly filled with the treated soil. Ten larvae of *Diabrotica balteata* in the $L_3$ stage are used and four maize seedlings are planted per beaker and the beakers are filled with soil. The filled beakers are covered with plastic film and kept at a temperature of about 24° C. and a relative humidity of about 50%. Six days after the start of the test, the soil contained in the beakers is sieved and the mortality of the larvae which remain is assessed.

Compounds according to Examples 1.2. exhibit good activity in this test.

3.17. Action against *Anthonomus grandis* (adults)

Two cotton plants in the 6-leaf stage, in pots, are each sprayed with wettable aqueous emulsion formulations containing 100 ppm of the test compound. After the spray coating has dried (about 1.5 hours) each plant is populated with 10 adult beetles (*Anthonomus grandis*). Plastic cylinders, covered at the top with gauze, are then slipped over the treated plants populated with the test insects to prevent the beetles from migrating from the plants. The treated plants are kept at 25° C. and about 60% relative humidity. Evaluation is made after 2, 3, 4 and 5 days to determine the percentage mortality of the beetles (percentage in dorsal position) and the anti-feeding action as compared with untreated controls.

Compounds according to Examples 1.2. exhibit good activity in this test.

3.18. Action against *Dermanyssus gallinae*

2 to 3 ml of a solution containing 100 ppm of the test compound and about 200 mites in various development stages are placed in a glass container open at the top. The container is then closed with a cotton wool plug, shaken for 10 minutes until the mites are completely wet and then briefly inverted in order that the remaining test solution can be absorbed by the cotton wool. After 3 days the percentage mortality of the mites is determined by counting the dead insects.

Compounds according to Examples 1.2. are 80-100% effective (mortality).

3.19. Action against *Blattella germanica*

An amount of a 0.1% acetonic solution of the test compound equivalent to a rate of application of 2 g/m² is introduced into a Petri dish 10 cm in diameter. When the solvent has evaporated, 20 *Blattella germanica* nymphs (final nymph stage) are placed in the prepared dish and exposed to the action of the test compound for 2 hours. The nymphs are then narcotised with $CO_2$, placed in a fresh Petri dish and kept in the dark at 25° C. and 50 to 70% humidity. After 48 hours the insecticidal action is evaluated by determining the mortality rate.

Compounds according to Examples 1.2. exhibit good activity in this test.

What is claimed is:

1. Compounds of formula I

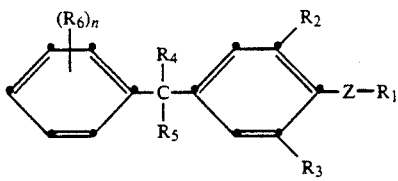 (I)

in which $R_1$ is $C_1$-$C_8$alkyl, $C_1$-$C_8$alkyl mono- or poly-substituted by halogen and/or by $C_1$-$C_6$alkoxy, $C_3$-$C_8$-cycloalkyl, $C_3$-$C_8$cycloalkyl mono- or poly-substituted by $C_1$-$C_3$alkyl, or is $C_3$-$C_8$cycloalkyl-$C_1$-$C_4$alkyl; each of $R_2$ and $R_3$ is $C_1$-$C_6$alkyl, $C_5$-$C_6$cycloalkyl or $C_5$-$C_6$-cycloalkenyl; each of $R_4$ and $R_5$ is hydrogen or $C_1$-$C_4$alkyl; each $R_6$ is halogen, $C_1$-$C_4$alkyl, $C_1$-$C_4$alkoxy, $C_1$-$C_4$haloalkyl, $C_1$-$C_4$haloalkoxy or a $-(CH=CH)_2-$, $-(CH_2)_3-$ or $-(CH_2)_4-$ bridge in the 2,3- or 3,4-position; n is 0, 1 or 2; Z is —NH—CS—NH—, and $R_7$ is $C_1$-$C_{10}$alkyl or $C_3$-$C_5$alkenyl, and salts thereof with organic or inorganic acids.

2. Compounds of formula I according to claim 1, in which $R_1$ is $C_1$-$C_6$alkyl, $C_1$-$C_6$alkyl mono- or poly-substituted by halogen and/or by $C_1$-$C_3$alkoxy, or $C_5$-$C_6$-cycloalkyl; each of $R_2$ and $R_3$ is $C_1$-$C_5$alkyl or $C_5$-$C_6$cycloalkyl; each of $R_4$ and $R_5$ is hydrogen or $C_1$-$C_3$alkyl; $R_6$ is halogen, methyl, methoxy, trifluoromethyl or trifluoromethoxy; n is 0 or 1; Z is —NH—CS—NH—; and $R_7$ is $C_1$-$C_6$alkyl or $C_3$-$C_4$alkenyl.

3. Compounds of formula I according to claim 2, in which $R_1$ is $C_1$-$C_5$alkyl or cyclopentyl; each of $R_2$ and $R_3$ is $C_3$-$C_5$alkyl or $C_5$-$C_6$cycloalkyl; each of $R_4$ and $R_5$ is hydrogen or methyl; $R_6$ is fluorine, chlorine or methyl; n is 0 or 1; Z is —NH—CS—NH—; and $R_7$ is $C_1$-$C_3$alkyl or allyl.

4. Compounds of formula I according to claim 3, in which $R_1$ is $C_3$-$C_5$alkyl or cyclopentyl; each of $R_2$ and $R_3$ is $C_3$-$C_5$alkyl; each of $R_4$ and $R_5$ is hydrogen or methyl; n is 0; and Z is —NH—CS—NH—.

5. The compounds according to claim 1 of the formulae

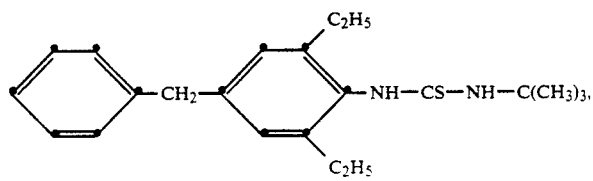

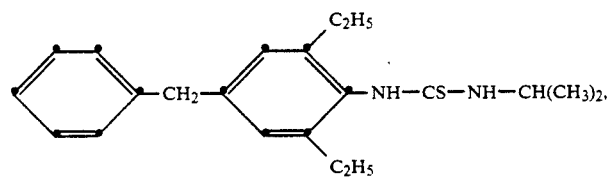

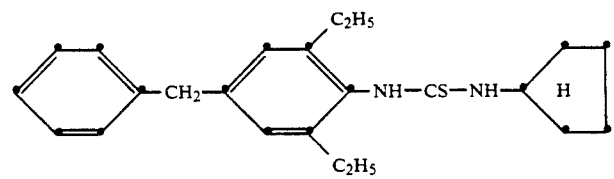

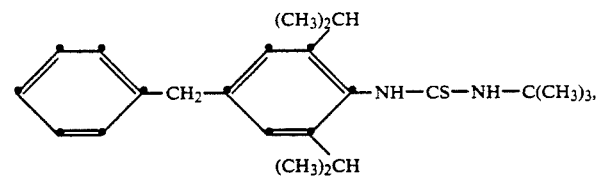

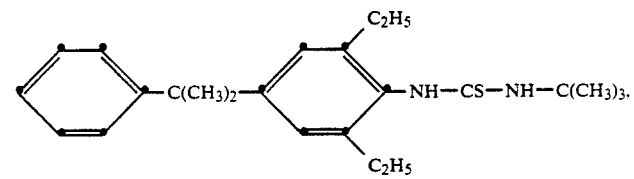

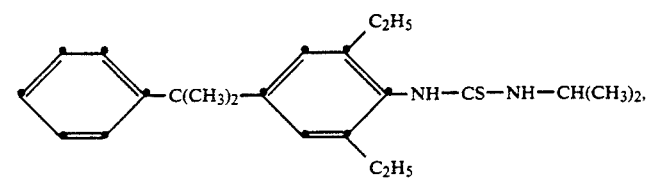

-continued
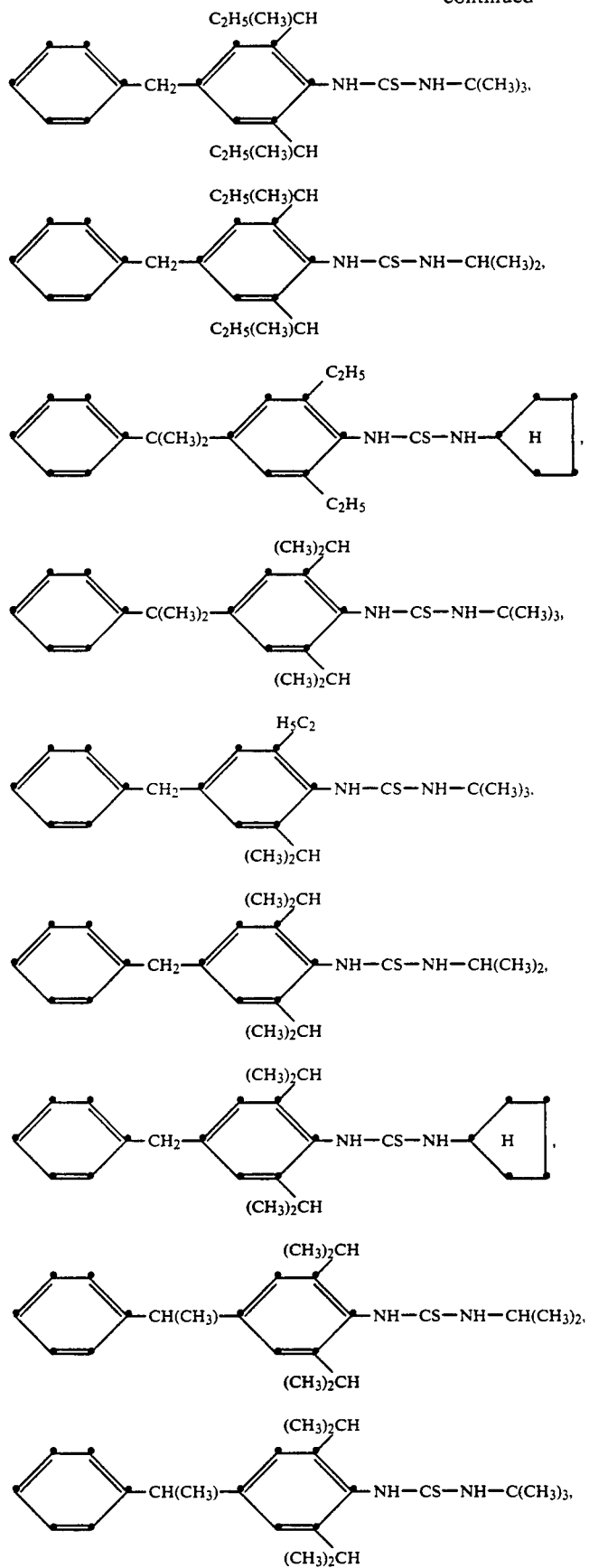

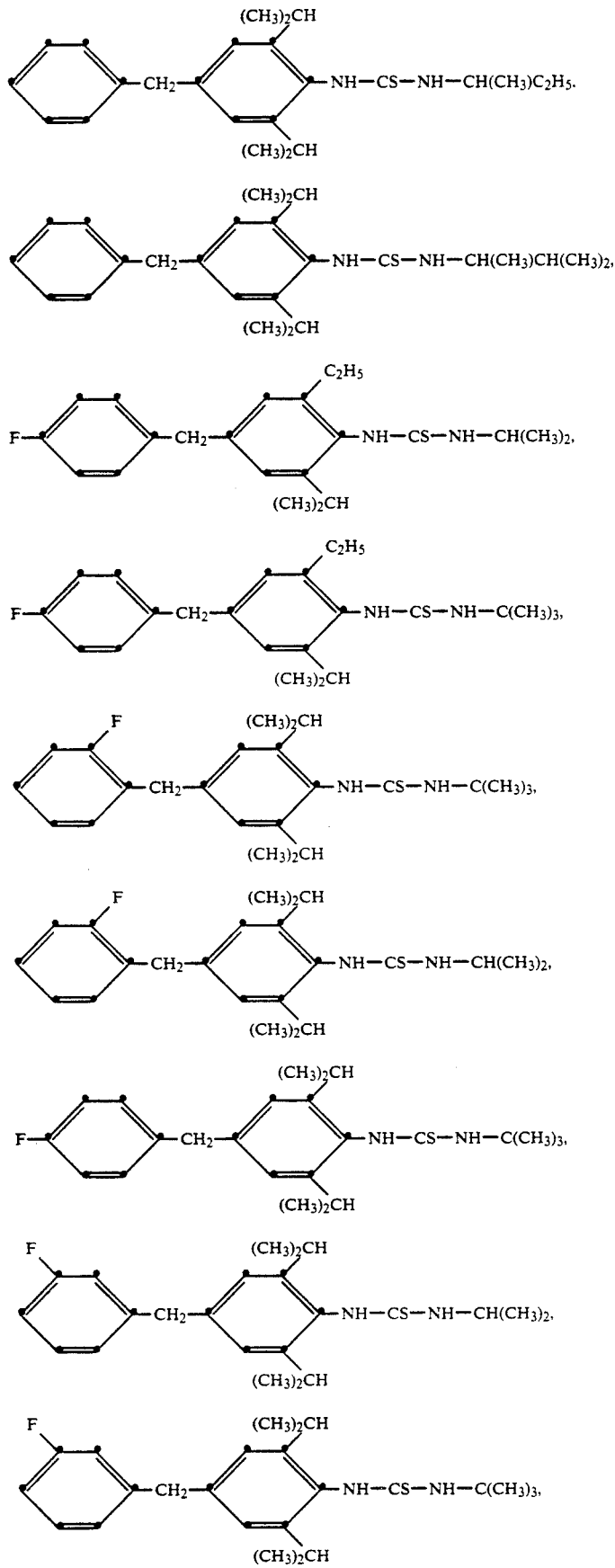

-continued

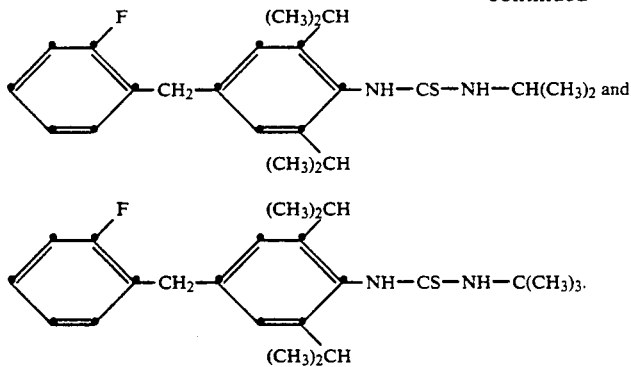

6. A pesticidal composition which comprises as active component a pesticidally effective amount of a compound of formula I

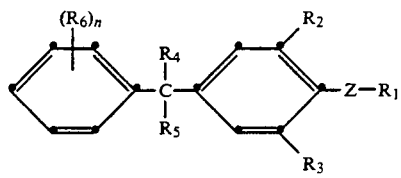

in which $R_1$ is $C_1$-$C_8$alkyl, $C_1$-$C_8$alkyl mono- or polysubstituted by halogen and/or by $C_1$-$C_6$alkoxy, $C_3$-$C_8$-cycloalkyl, $C_3$-$C_8$cycloalkyl mono- or poly-substituted by $C_1$-$C_3$alkyl, or is $C_3$-$C_8$cycloalkyl-$C_1$-$C_4$alkyl; each of $R_2$ and $R_3$ is $C_1$-$C_6$alkyl, $C_5$-$C_6$cycloalkyl or $C_5$-$C_6$-cycloalkenyl; each of $R_4$ and $R_5$ is hydrogen or $C_1$-$C_4$alkyl; each $R_6$ is halogen, $C_1$-$C_4$alkyl, $C_1$-$C_4$alkoxy, $C_1$-$C_4$haloalkyl, $C_1$-$C_4$haloalkoxy or a $-(CH=CH)_2$, $-(CH_2)_3$ or $-(CH_2)_4$ bridge in the 2,3- or 3,4-position; n is 0, 1 or 2; Z is —NH—CS—NH—, and $R_7$ is $C_1$-$C_{10}$alkyl or $C_3$-$C_5$alkenyl, or one of the salts thereof with an organic or inorganic acid together with suitable carriers and/or adjuvants.

7. A pesticidal composition according to claim 6, which comprises as active component a compound of formula I in which $R_1$ is $C_1$-$C_6$alkyl, $C_1$-$C_6$alkyl mono- or poly-substituted by halogen and/or by $C_1$-$C_3$alkoxy, or $C_5$-$C_6$cycloalkyl; each of $R_2$ and $R_3$ is $C_1$-$C_5$alkyl or $C_5$-$C_6$cycloalkyl; each of $R_4$ and $R_5$ is hydrogen or $C_1$-$C_3$alkyl; $R_6$ is halogen, methyl, methoxy, trifluoromethyl or trifluoromethoxy; n is 0 or 1; Z is —NH—C-S—NH—, and $R_7$ is $C_1$-$C_6$alkyl or $C_3$-$C_4$alkenyl.

8. A pesticidal composition according to claim 7, which comprises as active component at least one compound of formula I in which $R_1$ is $C_1$-$C_5$alkyl or cyclopentyl; each of $R_2$ and $R_3$ is $C_3$-$C_5$alkyl or $C_5$-$C_6$cycloalkyl; each of $R_4$ and $R_5$ is hydrogen or methyl; $R_6$ is fluorine, chlorine or methyl; n is 0 or 1; Z is —NH—C-S—NH—, and $R_7$ is $C_1$-$C_3$alkyl or allyl.

9. A pesticidal composition according to claim 8, which comprises as active component a compound of formula I in which $R_1$ is $C_3$-$C_5$alkyl or cyclopentyl; each of $R_2$ and $R_3$ is $C_3$-$C_5$alkyl; each of $R_4$ and $R_5$ is hydrogen or methyl; n is 0; and Z is —NH—C-S—NH—.

10. A method of controlling pests in and on animals and plants, which comprises bringing the pests in their various stages of development into contact with a compound of formula I

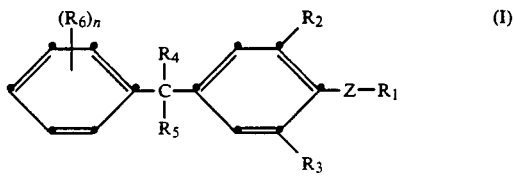

in which $R_1$ is $C_1$-$C_8$alkyl, $C_1$-$C_8$alkyl mono- or polysubstituted by halogen and/or by $C_1$-$C_6$alkoxy, $C_3$-$C_8$-cycloalkyl, $C_3$-$C_8$cycloalkyl mono- or poly-substituted by $C_1$-$C_3$alkyl, or is $C_3$-$C_8$cycloalkyl-$C_1$-$C_4$alkyl; each of $R_2$ and $R_3$ is $C_1$-$C_6$alkyl, $C_5$-$C_6$cycloalkyl or $C_5$-$C_6$-cycloalkenyl; each of $R_4$ and $R_5$ is hydrogen or $C_1$-$C_4$alkyl; each $R_6$ is halogen, $C_1$-$C_4$alkyl, $C_1$-$C_4$alkoxy, $C_1$-$C_4$haloalkyl, $C_1$-$C_4$haloalkoxy or a $-(CH=CH)_2$, $-(CH_2)_3$ or $-(CH_2)_4$ bridge in the 2,3- or 3,4-position; n is 0, 1 or 2; Z is —NH—CS—NH—, and $R_7$ is $C_1$-$C_{10}$alkyl or $C_3$-$C_5$alkenyl, or with one of the salts thereof with an organic or inorganic acid.

11. A method according to claim 10 for controlling insects and arachnids.

* * * * *